United States Patent [19]
Mori et al.

[11] Patent Number: 6,093,535
[45] Date of Patent: Jul. 25, 2000

[54] METHOD FOR IDENTIFYING ATTENUATED CHICKENPOX VIRUS OKA STRAIN OR STRAIN ORIGINATING THEREIN AND ACCEPTABLE AS ATTENUATED CHICKENPOX VACCINE VIRUS

[75] Inventors: Chisato Mori, Nakamura; Rie Takahara; Juichiro Osame, both of Mitoyo-gun; Yasuyuki Gomi, Kanonji; Isao Fuke, Takamatsu, all of Japan

[73] Assignee: The Research Foundation for Microbial Diseases of Osaka University, Osaka, Japan

[21] Appl. No.: 08/983,045

[22] PCT Filed: May 15, 1997

[86] PCT No.: PCT/JP97/01646

§ 371 Date: Jan. 15, 1998

§ 102(e) Date: Jan. 15, 1998

[87] PCT Pub. No.: WO97/43420

PCT Pub. Date: Nov. 20, 1997

[30] Foreign Application Priority Data

May 15, 1996 [JP] Japan ..................................... 8-158795

[51] Int. Cl.[7] .............................. C12Q 1/70; C12P 19/34; C12N 7/00; C07H 21/04
[52] U.S. Cl. .......................... 435/5; 435/91.2; 435/320.1; 424/186.1; 424/230.1; 536/24.33
[58] Field of Search ........................... 435/5, 320.1, 91.2; 424/186.1, 230.1; 536/24.33

[56] References Cited

U.S. PATENT DOCUMENTS 3,985,615  10/1976  Kubo ......................................... 435/5

FOREIGN PATENT DOCUMENTS 53-041202  1/1978  Japan .
6-189752  12/1994  Japan .

OTHER PUBLICATIONS

Davison et al., *J. Gen. Virol.*, vol. 67, pp. 1759–1816 (1986).
Kinchington et al., *Journal of Virology,*, vol. 59, No. 3, pp. 660–668 (Sep. 1986).
Hondo et al., *Japanese Journal of Experimental Medicine*, vol. 59, No. 6, pp. 233–237 (1989).
LaRussa et al., *Journal of Virology*, vol. 66, No. 2, pp. 1016–1020 (Feb. 1992).
Takada et al., *Journal of Clinical Microbiology*, vol. 33, No. 3, pp. 658–660 (Mar. 1995).
Hayakawa et al., *The Journal of Infectious Diseases*, vol. 149, No. 6, pp. 956–963 (Jun. 1984).
Orita et al., *Proc. Natl. Acad. Sci. USA*, vol. 86, pp. 2766–2770 (Apr. 1989).
Adams et al. Jan. 1989 Journal of Medical Virology 29: 38–45.
Gelb et al. Jan. 1990 Advances in Experimental Medicine and Biology 278: 59–69.
Hayakawa et al. Jan. 1984 Journal of Infectious Diseases 149:6 956–963.
Hayakawa et al. Jan. 1986 J Gen Virol. 67:1817–1829.
Kinchington et al. Jan. 1990 Advances in Experimental Medicine and Biology 278:83–91.
Shiraki et al. Jan. 1991 J Med Virol. 33: 128–132.
Sequence alignments for Davison and Kinchington, Feb. 1999.
Takada et al. Jan. 1995 J Clin Microbiol. 33:658–660.
Kinchington et al. Jan. 1986 J Virology 59: 660–668.
Davison et al. Jan. 1986 J Gen Virol 67:1759–1816.

*Primary Examiner*—Donna C. Wortman
*Assistant Examiner*—Mary K Zeman
*Attorney, Agent, or Firm*—Birch, Stewart. Kolasch & Birch, LLP

[57] ABSTRACT

Disclosed is a method for exact identification of the attenuated varicella virus Oka strain or a strain derived therefrom capable of functioning as an attenuated varicella live vaccine virus, which comprises analyzing the difference in the genomic DNA and fragments thereof between the Oka strain and a sample varicella strain, and determining whether or not a sample strain satisfies all of the following eight characteristics: the sizes of the HpaI-K fragment and the EcoRI-P fragment; the size of R2-487 region of Gene14 and the analysis by PCR-SSCP; the sizes of the restriction fragments obtained by digesting the R2-1764 fragment with AccIII; the absence or presence of a PstI cleavage site; the homology of the amino acid sequences coded by R2-487 coding region; and the homology of the amino acid sequences coded by the coding region of VZV Gene14. The method of the present invention is extremely useful for the quality control and quality assurance of attenuated varicella live vaccines. Also disclosed are an isolated virus strain which is substantially the same virus strain as identified by the above method; an attenuated varicella virus live vaccine comprising the same virus strain as identified by the above method; an attenuated varicella virus Oka strain antigen; and a pair of primers which are advantageously, effectively usable in the above method.

3 Claims, 7 Drawing Sheets

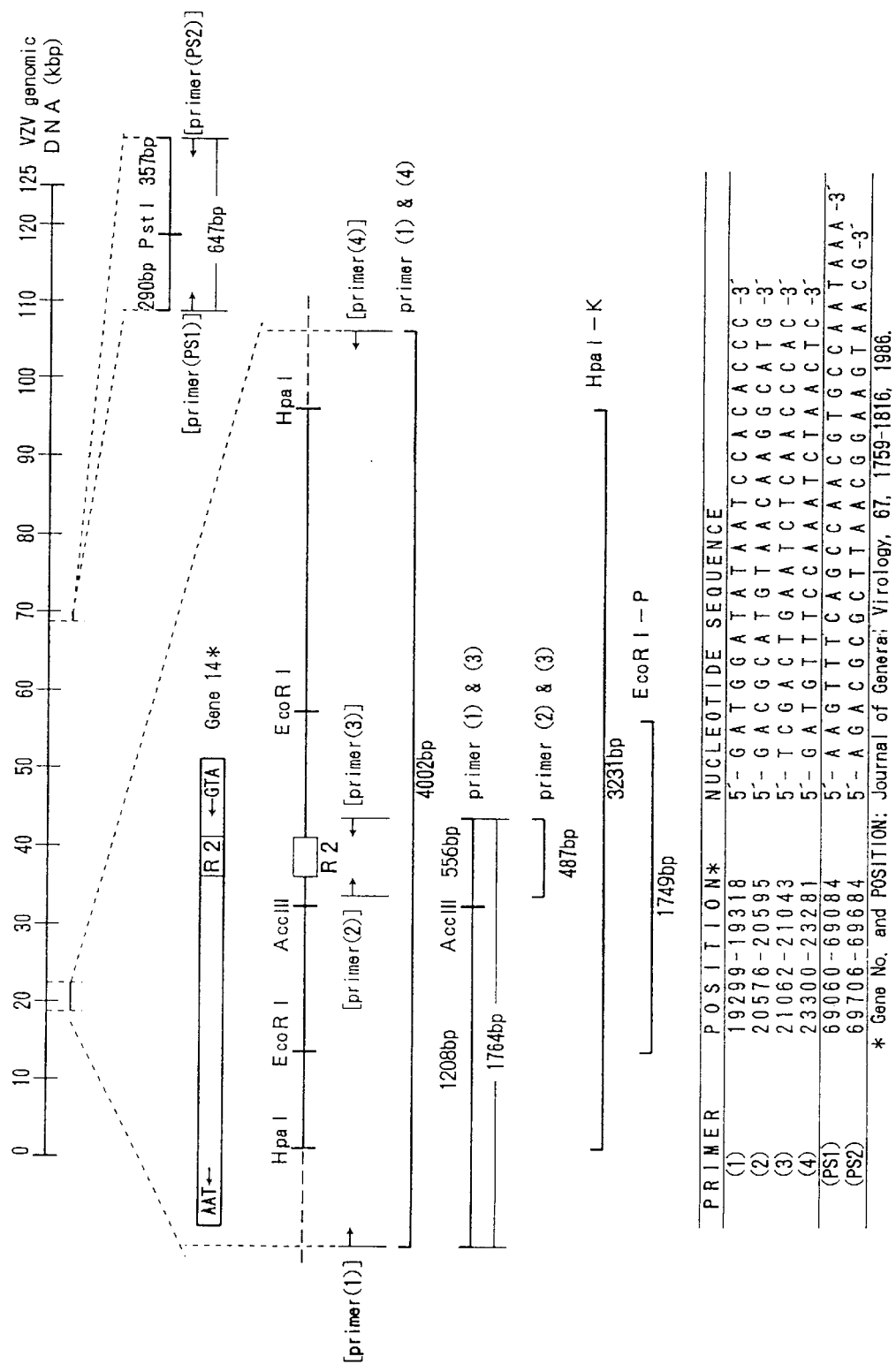

Fig. 2A

```
Oka      : ATGAAGCGGATACAAATAAATTTAATTTTAACGATCGCGTGTATACAATTATCGACTGAA   60
Davison  : ............................................................
Kinchin. : ............................................................

Oka      : TCTCAACCCACACCCGTAAGTATAATTGAATTATATACCTCGGCCGCTTCCCGAAAGCCC  120
Davison  : ..............C............................A...............
Kinchin. : ..............C............................A...............

Oka      : GATCCCGCCGTCGCGCCCACCTCGGCCGCTTCCCGAAAGCCCGATCCCGCCGTCGCGCCC  180
Davison  : ............................................................
Kinchin. : ............................................................

Oka      : ACCTCGGCCGCTTCCCGAAAGCCCGATCCCGCCGTCGCGCCCACCTCGGCCGCTTCCCGA  240
Davison  : ............................................................
Kinchin. : ............A...............................................

Oka      : AAGCCCGATCCCGCCGTCGCGCCCACCTCGGCCGCTACCCGAAATCCCGATCCCGCCGTC  300
Davison  : .............................................G..............
Kinchin. : .....................................T......G..............

Oka      : GCGCCCACCTCGGCCGCTTCCCGAAATCCCGATCCCGCCGTCGCGCCCACCTCGGCCGCT  360
Davison  : ....................G.......................................
Kinchin. : ............A.......G.......................................

Oka      : TCCCGAAATCCCGATCCCGCCGTCGCGCCCACCTCGGCCGCTACCCGAAAGCCCGATCCC  420
Davison  : A......G........................T...........................
Kinchin. : A...........................................................

Oka      : GCAGCCAACGCCCAACATTCACAACCACCTTTTCTATTTGAAAATATACAATGCGTTCAC  480
Davison  : .........A.....................A...........................
Kinchin. : ............................................................

Oka      : GGCGGAATACAATCCATACCCTATTTTCACACATTTATCATGCCTTGTTACATGCGTCTA  540
Davison  : ............................................................
Kinchin. : ............................................................
```

Fig. 2B

```
Oka       : ACGACCGGACAACAGGCGGCCTTTAAGCAGCAACAAAAAACATATGAACAATATTCTTTA    600
Davison   : ............................................................
Kinchin.  : ............................................................

Oka       : GATCCGGAAGGTTCAAATATAACAAGGTGGAAGTCGCTTATACGCCCCGATCTTCATATT    660
Davison   : ............................................................
Kinchin.  : ............................................................

Oka       : GAAGTTTGGTTTACGCGTCACCTTATAGATCCGCACCGTCAACTGGGCAATGCGTTAATA    720
Davison   : ............................................................
Kinchin.  : ............................................................

Oka       : CGCATGCCAGATTTACCGGTTATGTTATATAGCAACAGTGCCGATTTAAACTTAATAAAC    780
Davison   : ............................................................
Kinchin.  : ............................................................

Oka       : AACCCTGAGATATTTACACACGCTAAGGAAAATTATGTAATACCAGATGTTAAAACAACG    840
Davison   : ............................................................
Kinchin.  : ............................................................

Oka       : TCTGATTTTCTGTAACAATTTTATCTATGGATGCTACCACGGAGGGAACGTATATTTGG    900
Davison   : ............................................................
Kinchin.  : ............................................................

Oka       : CGAGTCGTTAATACAAAAACTAAGAACGTCATATCGGAACACAGTATTACAGTTACAACG    960
Davison   : ............................................................
Kinchin.  : ............................................................

Oka       : TATTATCGTCCAAATATTACCGTTGTCGGCGATCCAGTCTTAACCGGACAGACATACGCA    1020
Davison   : ............................................................
Kinchin.  : ............................................................

Oka       : GCCTACTGTAACGTATCAAAGTATTATCCACCGCACTCGGTACGTGTTCGGTGGACTTCA    1080
Davison   : ............................................................
Kinchin.  : ............................................................

Oka       : AGGTTTGGTAACATCGGAAAAAATTTTATAACCGATGCAATACAAGAATATGCCAATGGA    1140
Davison   : ............................................................
Kinchin.  : ............................................................
```

Fig.2C

```
Oka      : TTATTTAGTTATGTTTCGGCGGTACGAATTCCACAGCAAAAACAAATGGATTACCCACCC   1200
Davison  : ............................................................
Kinchin. : ............................................................

Oka      : CCAGCCATCCAATGTAATGTTTTATGGATTCGGGATGGCGTCTCTAATATGAAATATTCT   1260
Davison  : ............................................................
Kinchin. : ............................................................

Oka      : GCTGTCGTTACCCCTGACGTCTATCCATTTCCCAACGTGTCTATAGGTATTATTGATGGA   1320
Davison  : ............................................................
Kinchin. : ............................................................

Oka      : CACATAGTATGTACGGCAAAATGTGTGCCACGTGGCGTTGTACATTTCGTATGGTGGGTT   1380
Davison  : ............................................................
Kinchin. : ............................................................

Oka      : AACGATTCTCCCATCAACCACGAAAACAGTGAGATTACTGGGGTGTGTGATCAAAACAAA   1440
Davison  : .............T..............................................
Kinchin. : .............T..............................................

Oka      : CGGTTTGTAAACATGCAAAGTTCTTGTCCAACATCGGAACTCGACGGACCTATCACCTAT   1500
Davison  : ............................................................
Kinchin. : ............................................................

Oka      : TCGTGTCATCTAGATGGTTACCCTAAAAAATTCCCTCCGTTTTCGGCCGTTTATACCTAC   1560
Davison  : ............................................................
Kinchin. : ............................................................

Oka      : GATGCATCTACCTACGCCACTACATTTTCCGTTGTAGCAGTTATAATTGGTGTGATATCT   1620
Davison  : ............................................................
Kinchin. : ............................................................

Oka      : ATCCTTGGGACATTGGGTCTTATCGCAGTTATCGCAACCCTATGCATCCGTTGCTGTTCA   1680
Davison  : ............................................................
Kinchin. : ............................................................

Oka      : TAA   1683
Davison  : ...
Kinchin. : ...
```

Fig. 3A

```
Oka     : Met Lys Arg Ile Gln Ile Asn Leu Ile Leu Thr Ile Ala Cys Ile Gln Leu Ser Thr Glu   20
Davison : .   .   .   .   .   .   .   .   .   .   .   .   .   .   .   .   .   .   .   .
Kinchin.: .   .   .   .   .   .   .   .   .   .   .   .   .   .   .   .   .   .   .   .

Oka     : Ser Gln Pro Thr Pro Val Ser Ile Ile Glu Leu Tyr Thr Ser Ala Ala Ser Arg Lys Pro   40
Davison : .   .   .   .   .   .   .   .   .   Thr .   .   .   .   .   .   Thr .   .   .
Kinchin.: .   .   .   .   .   .   .   .   .   Thr .   .   .   .   .   .   Thr .   .   .

Oka     : Asp Pro Ala Val Ala Pro Thr Ser Ala Ala Ser Arg Lys Pro Asp Pro Ala Val Ala Pro   60
Davison : .   .   .   .   .   .   .   .   .   .   .   .   .   .   .   .   .   .   .   .
Kinchin.: .   .   .   .   .   .   .   .   .   .   .   .   .   .   .   .   .   .   .   .

Oka     : Thr Ser Ala Ala Ser Arg Lys Pro Asp Pro Ala Val Ala Pro Thr Ser Ala Ala Ser Arg   80
Davison : .   .   .   .   .   .   .   .   .   .   .   .   .   .   .   .   .   .   .   .
Kinchin.: .   .   .   .   Thr .   .   .   .   .   .   .   .   .   .   .   .   .   .   .

Oka     : Lys Pro Asp Pro Ala Val Ala Pro Thr Ser Ala Ala Thr Arg Asn Pro Asp Pro Ala Val  100
Davison : .   .   .   .   .   .   .   .   .   .   .   .   .   .   Lys .   .   .   .   .
Kinchin.: .   .   .   .   .   .   .   .   .   .   .   Ser .   Lys .   .   .   .   .   .

Oka     : Ala Pro Thr Ser Ala Ala Ser Arg Asn Pro Asp Pro Ala Val Ala Pro Thr Ser Ala Ala  120
Davison : .   .   .   .   .   .   .   .   Lys .   .   .   .   .   .   .   .   .   .   .
Kinchin.: .   .   .   .   .   .   Thr .   Lys .   .   .   .   .   .   .   .   .   .   .

Oka     : Ser Arg Asn Pro Asp Pro Ala Val Ala Pro Thr Ser Ala Ala Thr Arg Lys Pro Asp Pro  140
Davison : Thr .   Lys .   .   .   .   .   .   .   .   .   .   .   Ser .   .   .   .   .
Kinchin.: Thr .   .   .   .   .   .   .   .   .   .   .   .   .   .   .   .   .   .   .

Oka     : Ala Ala Asn Ala Gln His Ser Gln Pro Pro Phe Leu Phe Glu Asn Ile Gln Cys Val His  160
Davison : .   .   .   Thr .   .   .   .   .   .   .   .   Tyr .   .   .   .   .   .   .
Kinchin.: .   .   .   .   .   .   .   .   .   .   .   .   .   .   .   .   .   .   .   .

Oka     : Gly Gly Ile Gln Ser Ile Pro Tyr Phe His Thr Phe Ile Met Pro Cys Tyr Met Arg Leu  180
Davison : .   .   .   .   .   .   .   .   .   .   .   .   .   .   .   .   .   .   .   .
Kinchin.: .   .   .   .   .   .   .   .   .   .   .   .   .   .   .   .   .   .   .   .

Oka     : Thr Thr Gly Gln Gln Ala Ala Phe Lys Gln Gln Gln Lys Thr Tyr Glu Gln Tyr Ser Leu  200
Davison : .   .   .   .   .   .   .   .   .   .   .   .   .   .   .   .   .   .   .   .
Kinchin.: .   .   .   .   .   .   .   .   .   .   .   .   .   .   .   .   .   .   .   .

Oka     : Asp Pro Glu Gly Ser Asn Ile Thr Arg Trp Lys Ser Leu Ile Arg Pro Asp Leu His Ile  220
Davison : .   .   .   .   .   .   .   .   .   .   .   .   .   .   .   .   .   .   .   .
Kinchin.: .   .   .   .   .   .   .   .   .   .   .   .   .   .   .   .   .   .   .   .

Oka     : Glu Val Trp Phe Thr Arg His Leu Ile Asp Pro His Arg Gln Leu Gly Asn Ala Leu Ile  240
Davison : .   .   .   .   .   .   .   .   .   .   .   .   .   .   .   .   .   .   .   .
Kinchin.: .   .   .   .   .   .   .   .   .   .   .   .   .   .   .   .   .   .   .   .

Oka     : Arg Met Pro Asp Leu Pro Val Met Leu Tyr Ser Asn Ser Ala Asp Leu Asn Leu Ile Asn  260
Davison : .   .   .   .   .   .   .   .   .   .   .   .   .   .   .   .   .   .   .   .
Kinchin.: .   .   .   .   .   .   .   .   .   .   .   .   .   .   .   .   .   .   .   .
```

Fig. 3B

```
Oka      : Asn Pro Glu Ile Phe Thr His Ala Lys Glu Asn Tyr Val Ile Pro Asp Val Lys Thr Thr  280
Davison  :  ·   ·   ·   ·   ·   ·   ·   ·   ·   ·   ·   ·   ·   ·   ·   ·   ·   ·   ·   ·
Kinchin. :  ·   ·   ·   ·   ·   ·   ·   ·   ·   ·   ·   ·   ·   ·   ·   ·   ·   ·   ·   ·

Oka      : Ser Asp Phe Ser Val Thr Ile Leu Ser Met Asp Ala Thr Thr Glu Gly Thr Tyr Ile Trp  300
Davison  :  ·   ·   ·   ·   ·   ·   ·   ·   ·   ·   ·   ·   ·   ·   ·   ·   ·   ·   ·   ·
Kinchin. :  ·   ·   ·   ·   ·   ·   ·   ·   ·   ·   ·   ·   ·   ·   ·   ·   ·   ·   ·   ·

Oka      : Arg Val Val Asn Thr Lys Thr Lys Asn Val Ile Ser Glu His Ser Ile Thr Val Thr Thr  320
Davison  :  ·   ·   ·   ·   ·   ·   ·   ·   ·   ·   ·   ·   ·   ·   ·   ·   ·   ·   ·   ·
Kinchin. :  ·   ·   ·   ·   ·   ·   ·   ·   ·   ·   ·   ·   ·   ·   ·   ·   ·   ·   ·   ·

Oka      : Tyr Tyr Arg Pro Asn Ile Thr Val Val Gly Asp Pro Val Leu Thr Gly Gln Thr Tyr Ala  340
Davison  :  ·   ·   ·   ·   ·   ·   ·   ·   ·   ·   ·   ·   ·   ·   ·   ·   ·   ·   ·   ·
Kinchin. :  ·   ·   ·   ·   ·   ·   ·   ·   ·   ·   ·   ·   ·   ·   ·   ·   ·   ·   ·   ·

Oka      : Ala Tyr Cys Asn Val Ser Lys Tyr Tyr Pro Pro His Ser Val Arg Val Arg Trp Thr Ser  360
Davison  :  ·   ·   ·   ·   ·   ·   ·   ·   ·   ·   ·   ·   ·   ·   ·   ·   ·   ·   ·   ·
Kinchin. :  ·   ·   ·   ·   ·   ·   ·   ·   ·   ·   ·   ·   ·   ·   ·   ·   ·   ·   ·   ·

Oka      : Arg Phe Gly Asn Ile Gly Lys Asn Phe Ile Thr Asp Ala Ile Gln Glu Tyr Ala Asn Gly  380
Davison  :  ·   ·   ·   ·   ·   ·   ·   ·   ·   ·   ·   ·   ·   ·   ·   ·   ·   ·   ·   ·
Kinchin. :  ·   ·   ·   ·   ·   ·   ·   ·   ·   ·   ·   ·   ·   ·   ·   ·   ·   ·   ·   ·

Oka      : Leu Phe Ser Tyr Val Ser Ala Val Arg Ile Pro Gln Gln Lys Gln Met Asp Tyr Pro Pro  400
Davison  :  ·   ·   ·   ·   ·   ·   ·   ·   ·   ·   ·   ·   ·   ·   ·   ·   ·   ·   ·   ·
Kinchin. :  ·   ·   ·   ·   ·   ·   ·   ·   ·   ·   ·   ·   ·   ·   ·   ·   ·   ·   ·   ·

Oka      : Pro Ala Ile Gln Cys Asn Val Leu Trp Ile Arg Asp Gly Val Ser Asn Met Lys Tyr Ser  420
Davison  :  ·   ·   ·   ·   ·   ·   ·   ·   ·   ·   ·   ·   ·   ·   ·   ·   ·   ·   ·   ·
Kinchin. :  ·   ·   ·   ·   ·   ·   ·   ·   ·   ·   ·   ·   ·   ·   ·   ·   ·   ·   ·   ·

Oka      : Ala Val Val Thr Pro Asp Val Tyr Pro Phe Pro Asn Val Ser Ile Gly Ile Ile Asp Gly  440
Davison  :  ·   ·   ·   ·   ·   ·   ·   ·   ·   ·   ·   ·   ·   ·   ·   ·   ·   ·   ·   ·
Kinchin. :  ·   ·   ·   ·   ·   ·   ·   ·   ·   ·   ·   ·   ·   ·   ·   ·   ·   ·   ·   ·

Oka      : His Ile Val Cys Thr Ala Lys Cys Val Pro Arg Gly Val Val His Phe Val Trp Trp Val  460
Davison  :  ·   ·   ·   ·   ·   ·   ·   ·   ·   ·   ·   ·   ·   ·   ·   ·   ·   ·   ·   ·
Kinchin. :  ·   ·   ·   ·   ·   ·   ·   ·   ·   ·   ·   ·   ·   ·   ·   ·   ·   ·   ·   ·

Oka      : Asn Asp Ser Pro Ile Asn His Glu Asn Ser Glu Ile Thr Gly Val Cys Asp Gln Asn Lys  480
Davison  :  ·   ·   ·   ·   ·   ·   ·   ·   ·   ·   ·   ·   ·   ·   ·   ·   ·   ·   ·   ·
Kinchin. :  ·   ·   ·   ·   ·   ·   ·   ·   ·   ·   ·   ·   ·   ·   ·   ·   ·   ·   ·   ·

Oka      : Arg Phe Val Asn Met Gln Ser Ser Cys Pro Thr Ser Glu Leu Asp Gly Pro Ile Thr Tyr  500
Davison  :  ·   ·   ·   ·   ·   ·   ·   ·   ·   ·   ·   ·   ·   ·   ·   ·   ·   ·   ·   ·
Kinchin. :  ·   ·   ·   ·   ·   ·   ·   ·   ·   ·   ·   ·   ·   ·   ·   ·   ·   ·   ·   ·

Oka      : Ser Cys His Leu Asp Gly Tyr Pro Lys Lys Phe Pro Pro Phe Ser Ala Val Tyr Thr Tyr  520
Davison  :  ·   ·   ·   ·   ·   ·   ·   ·   ·   ·   ·   ·   ·   ·   ·   ·   ·   ·   ·   ·
Kinchin. :  ·   ·   ·   ·   ·   ·   ·   ·   ·   ·   ·   ·   ·   ·   ·   ·   ·   ·   ·   ·
```

Fig.3c

```
Oka     : Asp Ala Ser Thr Tyr Ala Thr Thr Phe Ser Val Val Ala Val Ile Ile Gly Val Ile Ser  540
Davison : .   .   .   .   .   .   .   .   .   .   .   .   .   .   .   .   .   .   .   .
Kinchin.: .   .   .   .   .   .   .   .   .   .   .   .   .   .   .   .   .   .   .   .

Oka     : Ile Leu Gly Thr Leu Gly Leu Ile Ala Val Ile Ala Thr Leu Cys Ile Arg Cys Cys Ser  560
Davison : .   .   .   .   .   .   .   .   .   .   .   .   .   .   .   .   .   .   .   .
Kinchin.: .   .   .   .   .   .   .   .   .   .   .   .   .   .   .   .   .   .   .   .
```

METHOD FOR IDENTIFYING ATTENUATED CHICKENPOX VIRUS OKA STRAIN OR STRAIN ORIGINATING THEREIN AND ACCEPTABLE AS ATTENUATED CHICKENPOX VACCINE VIRUS

The application claims the benefit under 35 U.S.C. §371 of prior PCT International Application No. PCT/JP97/01646 which has an international filing date of May 15, 1997 which designated the United States of America, the entire contents of which are hereby incorporated by reference.

BACKGROUND OF THE INVENTION

1. Field of the Invention

The present invention relates to a method for identifying the attenuated varicella virus Oka strain. More particularly, the present invention relates to a method for identifying the attenuated varicella virus Oka strain or a strain derived therefrom capable of functioning as an attenuated varicella live vaccine virus, and an isolated virus strain which is substantially the same virus strain as identified as the attenuated varicella virus Oka strain or a strain derived therefrom by the above method. The present invention also relates to an attenuated varicella virus Oka strain antigen. The present invention further relates to a pair of novel primers which are advantageously, effectively usable in the method of the present invention.

2. Prior Art

As is well known, attenuated live varicella vaccines used today are manufactured from a seed strain of varicella-zoster virus (hereinafter, frequently referred to simply as "varicella virus") which is a virus derived from the attenuated varicella virus Oka strain (see Examined Japanese Patent Application Publication No. 53-41202 and U.S. Pat. No. 3,985,615), and the attenuated live vaccines are used widely throughout the world {Requirements for Varicella Vaccine (Live) Adopted 1984: WHO Technical Report Series, No. 725, pp. 102–124, 1985}. To ensure the safety and effectiveness of the vaccine, the number of passages of a virus used for producing the vaccine is under the control of a seed lot system, taking into consideration the potential genetic mutation which is likely to occur during the passage. That is, the manufacturers are under an obligation to produce varicella vaccines only from the virus derived from the approved seed virus for the live varicella vaccine, wherein the number of passages of the virus is not more than 10 as counted from the approved seed virus which is counted as 0 passage. In other words, the quality control and quality assurance of the attenuated live varicella vaccine rely upon the fulfillment of the seed lot system by the manufacturers, and the quality of the vaccine has not been determined by a direct genetic analysis of a seed virus genomic DNA or a vaccine virus genomic DNA.

Further, from the viewpoint of epidemiology which involves a tracing of the effects of a varicella vaccine and a post-market surveillance (PMS), the virological difference between the fresh wild-type strains isolated from the naturally infected varicella patients and the vaccine virus strains derived from the above-mentioned Oka strain needs to be determined, and various methods have been attempted for determination of the virological difference. Since the gene of a VZV genome and the structure of the gene were reported (Journal of General Virology, 67, 1759–1816, 1986), various determination methods of the virological difference based on the differences between the properties and characteristics of the strains, such as the difference in DNA sequence between the different VZV strains (Journal of Virology, 59, 660–668, 1986), the difference in the absence or presence of a restriction enzyme PstI cleavage site (Japanese Journal of Experimental Medicine, 59, 233–237, 1989), the difference in RFLP (restriction fragment length polymorphism) of the PCR (polymerase chain reaction) product (Journal of Virology, 66, 1016–1020, 1992), and the difference in the absence or presence of a restriction enzyme PstI restriction site which is taken in combination with the difference in RFLP of the PCR product (Journal of Clinical Microbiology, 33, 658–660, 1995). However, all of these methods are not sufficient and cannot be used for exact identification of the Oka strain.

In other words, for quality control and quality assurance of the vaccine and from the viewpoint of epidemiology which involves a tracing of the effects of the vaccine and a PMS, it is critically important to identify or determine the above-mentioned attenuated varicella virus Oka strain or a strain derived therefrom capable of functioning as an attenuated varicella live vaccine virus (which Oka strain or a strain derived therefrom can be used as an active ingredient of an attenuated live varicella vaccine). However, a method reliable for such identification or determination has not been established, and a development of such a method has been earnestly desired in the art.

SUMMARY OF THE INVENTION

In the above situation, the present inventors have made extensive and intensive studies with a view toward developing a novel method for identifying, with exactness and speediness, the attenuated varicella virus Oka strain or a strain derived therefrom capable of functioning as an attenuated varicella live vaccine virus. The present inventors have performed an extensive genetic analysis to investigate the difference in genomic DNA between the attenuated varicella virus Oka strain (or a strain derived therefrom capable of functioning as an attenuated varicella live vaccine virus) and other varicella strains, such as a known varicella strain and a fresh wild-type strain. As a result, they have found that eight specific characteristics described below can be used for identifying the attenuated varicella virus Oka strain (or a strain derived therefrom capable of functioning as an attenuated varicella live vaccine virus) with exactness and speediness. That is, they have found that exact and speedy identification of the Oka strain or a useful strain derived therefrom can be made by determining whether or not a sample strain satisfies all of the eight characteristics. The present invention has been completed, based on this novel finding.

Therefore, it is an object of the present invention to provide a novel method for identifying the attenuated varicella virus Oka strain or a strain derived therefrom capable of functioning as an attenuated varicella live vaccine virus, with exactness and speediness.

It is another object of the present invention to provide an isolated virus strain which is substantially the same virus strain as identified, by the above-mentioned method, as the attenuated varicella virus Oka strain or a strain derived therefrom capable of functioning as an attenuated varicella live vaccine virus.

It is a further object of the present invention to provide an attenuated varicella live vaccine comprising, as an active ingredient, an isolated virus strain which is substantially the same virus strain as identified, by the above-mentioned method, as the attenuated varicella virus Oka strain or a strain derived therefrom capable of functioning as an attenuated varicella live vaccine virus.

Still a further object of the present invention is to provide an attenuated varicella virus Oka strain antigen comprising a contiguous sequence of at least a part of an amino acid sequence coded by a particular region of the attenuated varicella virus genomic DNA.

Still a further object of the present invention is to provide a pair of novel primers which can be advantageously, effectively used in the method of the present invention.

The foregoing and other objects, features and advantages of the present invention will be apparent to those skilled in the art from the following detailed description and the appended claims taken in connection with the accompanying sequence listing and drawings.

The Definition and Explanation of the Terminologies Used in the Present Invention (1) VZV: An abbreviation for "varicella-zoster virus" (hereinafter, frequently referred to simply as "varicella virus") which causes varicella-herpes zoster. The identification method of the present invention may be applied to a virus isolated from a patient suffering from either varicella or zoster.

(2) Varicella vaccine: A vaccine effective for preventing the infection with a VZV or the onset of the disease after the infection.

(3) Attenuated Oka strain: A strain which is equivalent to the attenuated varicella virus Oka strain (see Examined Japanese Patent Application Publication 53-41202 and U.S. Pat. No. 3,985,615). The attenuated Oka strain is deposited under the deposition number VR-795 on Mar. 14, 1975 with ATCC (American Type Culture Collection; 10801 University Boulevard, Mancossas, Va. 20110-2209 ).

(4) Attenuated varicella vaccine virus: A varicella virus derived from the approved seed virus for preparing the live varicella vaccine, wherein the number of passages of the virus is not more than 10 as counted from the approved seed virus which is counted as 0 passage (see WHO Technical Report Series No. 725, pp. 107–108, 1985). An attenuated varicella virus is useful as an active ingredient for a varicella vaccine.

(5) Gene numbers of VZV (Gene14 and Gene38) and the nucleotide numbers of the DNA: These numbers are based on the report by Davison and Scott (Journal of General Virology, 67, 1759–1816, 1986).

(6) The size of a restriction fragment {unit: base pair (bp)}: The size of a restriction fragment having cohesive ends which is obtained by digesting a VZV gene DNA sequence with a restriction enzyme is calculated from the cleavage sites of the restriction enzyme. For example, when the restriction enzyme E cleavage sites are two sites of the 10th nucleotide and the 60th nucleotide of the sequence, the size of the obtained restriction fragment E of the DNA is 60−10=50, namely, 50 bp.

(7) HK fragment: An abbreviation for HpaI-K shown in FIG. 1 (Journal of infectious Diseases, 149, 956–963, 1984; this means the K fragment obtained by digesting a VZV genomic DNA with the restriction enzyme HpaI).

(8) EP fragment: An abbreviation for EcoRI-P shown in FIG. 1 (Journal of Virology, 59, 660–668; this means the P fragment obtained by digesting a VZV genomic DNA with the restriction enzyme EcoRI).

(9) PCR-SSCP: An abbreviation for "Polymerase Chain Reaction-Single Strand Conformation Polymorphism" which is a method for analyzing a DNA fragment, which is amplified by PCR, in accordance with SSCP (Proceedings of National Academy of Science, USA, 86, 2766–2770, 1989).

(10) R2-487 region: A region of a VZV genome comprising the repetitive sequence R2 of Gene14, which region is obtained as a DNA fragment amplified by PCR using the PCR primers (2) and (3) shown in Table 1. The size of the R2-487 region of the attenuated varicella live vaccine virus Oka strain is 487 bp.

(11) R2-1764 region: A region of a VZV genome comprising the repetitive sequence R2 of Gene14, which region is obtained as a DNA fragment amplified by PCR using the PCR primers (1) and (3) shown in Table 1. The size of the R2-1764 region of the attenuated varicella live vaccine virus Oka strain is 1764 bp.

(12) Primers: The names and DNA sequences {described in a direction from left (5') to right (3')} of the PCR primers used in the present invention are shown in the following Table 1:

TABLE 1

| Names of the primers, and DNA sequences thereof | | |
|---|---|---|
| Primer (1): | 5'-GATGGATATAATCCACACCC-3' (sense strand) | SEQ ID NO:5 |
| Primer (2): | 5'-GACGCATGTAACAAGGCATG-3' (sense strand) | SEQ ID NO:6 |
| Primer (3): | 5'-TCGACTGAATCTCAACCCAC-3' (antisense strand) | SEQ ID NO:7 |
| Primer (4): | 5'-GATGTTTCCAAATCTAACTC-3' (antisense strand) | SEQ ID NO:8 |
| Primer (PS1): | 5'-AAGTTTCAGCCAACGTGCCAATAAA-3' (sense strand) | SEQ ID NO:9 |
| Primer (PS2): | 5'-AGACGCGCTTAACGGAAGTAACG-3' (antisense strand) | |

As mentioned above, the present inventors have made an investigation, by genetic analysis, on the difference in genomic DNA between the attenuated varicella virus Oka strain (or a strain derived therefrom capable of functioning as an attenuated varicella live vaccine virus) and other VZV strains, for example, known strains and fresh wild-type strains. The subjects of the genetic analysis can be summarized in (a) to (e) below (see FIG. 1 also):

(a) individually determining the sizes of the HK fragment and the EP fragment;

(b) amplifying the R2-1764 region by PCR to obtain a VZV genomic DNA fragment, and treating the obtained fragment with the restriction enzyme AccIII {A Practical Guide to Molecular Cloning, Second Edition (1988)} to confirm its cleavage into two parts, followed by determining the sizes of the two parts;

(c) amplifying the R2-487 region by PCR to obtain a VZV genomic DNA fragment and determining the size of the DNA fragment, wherein an analysis of the R2-487 region by PCR-SSCP and a determination of the nucleotide sequence of the region are also conducted;

(d) amplifying a part of Gene38 by PCR to obtain a VZV genomic DNA fragment, and treating the obtained fragment with the restriction enzyme PstI, followed by determination of the size of the fragment before and after the treatment to thereby determine whether the fragment is cleaved with PstI or not, wherein the analysis confirms the absence or presence of a restriction enzyme PstI cleavage site; and (e) amplifying the entire coding region of the VZV Gene14 by PCR, and determining the nucleotide sequence thereof.

The present invention was completed, based on the results of the above-mentioned analyses (a) to (e).

BRIEF DESCRIPTION OF THE SEQUENCE LISTING

SEQ ID NO. 1 is the nucleotide sequence of the R2-487 region of the attenuated Oka strain genomic DNA, and the amino acid sequence (162 amino acid residues) translated from the nucleotide sequence in accordance with the universal code (also set forth in SEQ ID NO:2);

SEQ ID NO. 3 is the nucleotide sequence of the entire coding region of Gene14 (1683 bp), and the amino acid sequence (560 amino acid residues) translated from the nucleotide sequence in accordance with the universal code (also set forth in SEQ ID No:4); and SEQ ID NOs. 5–10 are the PCR primers used for preparing the DNA fragments of the VZV genomic DNA which are used for identifying the attenuated varicella virus Oka strain.

BRIEF DESCRIPTION OF THE DRAWINGS

In the accompanying drawings:

FIG. 1 is a diagram of a VZV genomic DNA (approximately 125 kb) showing the location of Gene14, the location and size of the restriction fragments of the genomic DNA of the attenuated Oka strain, and the nucleotide sequence of the primers used in the present invention; and FIGS. 2A to 2C and FIGS. 3A to 3C show the comparison between the nucleotide and amino acid sequences of the attenuated Oka strain, the sequences disclosed by Davison and Scott (Journal of General Virology, 67, 1759–1816, 1986) and the sequences disclosed by Kinchington et al. (Journal of Virology, 59, 660–668, 1986). Each of the nucleotide sequences of the entire coding region of Gene14 are compared in FIGS. 2A to 2C, and each of the amino acid sequences translated from the nucleotide sequences in accordance with the universal code are compared in FIGS. 3A to 3C.

DETAILED DESCRIPTION OF THE INVENTION

According to the present invention, there is provided a novel method for accurately identifying the attenuated varicella virus Oka strain or a strain derived therefrom capable of functioning as an attenuated varicella live vaccine virus.

For easy understanding of the present invention, the essential features and various preferred embodiments of the present invention are enumerated below.

1. A method for identifying the attenuated varicella virus Oka strain or a strain derived therefrom capable of functioning as an attenuated varicella live vaccine virus, which comprises:

analyzing a genomic DNA and DNA fragments thereof of a sample varicella virus; and determining whether the analyzed genomic DNA and DNA fragments thereof of the sample varicella virus satisfy all of the following eight characteristics (A1) to (A8):

(A1) the size of the K fragment obtained by digesting the varicella virus genomic DNA with the restriction enzyme HpaI is 3231 bp;

(A2) the size of the P fragment obtained by digesting the varicella virus genomic DNA with the restriction enzyme EcoRI is 1749 bp;

(A3) when a DNA fragment which is amplified from the varicella virus genomic DNA by PCR using the PCR primer (1) of SEQ ID NO. 5 and the PCR primer (3) of SEQ ID NO. 7 is treated with the restriction enzyme AccIII, the DNA fragment is cleaved into two parts having sizes of 1208 bp and 556 bp, respectively;

(A4) a DNA fragment which is amplified from the varicella virus genomic DNA by PCR using the PCR primer (2) of SEQ ID NO. 6 and the PCR primer (3) of SEQ ID NO. 7 has a size of 487 bp;

(A5) the varicella virus genomic DNA and the attenuated varicella virus Oka strain genomic DNA exhibit substantially the same electrophoretic mobility with respect to a DNA fragment determined by PCR-SSCP wherein the PCR primer (2) of SEQ ID NO. 6 and the PCR primer (3) of SEQ ID NO. 7 are used in the PCR of the PCR-SSCP;

(A6) a DNA fragment which is amplified from the varicella virus genomic DNA by PCR using the PCR primer (PS1) of SEQ ID NO. 9 and the PCR primer (PS2) of SEQ ID NO. 10 lacks a restriction enzyme PstI cleavage site;

(A7) the homology between the 162 amino acid sequence coded by the varicella virus genomic DNA which sequence corresponds to the 162 amino acid sequence of SEQ ID NO. 1, and the 162 amino acid sequence of SEQ ID NO.1 is 98 to 100%; and (A8) the homology between the 560 amino acid sequence coded by the varicella virus genomic DNA which sequence corresponds to the 560 amino acid sequence of SEQ ID NO. 3, and the 560 amino acid sequence of SEQ ID NO.3 is 99 to 100%.

2. An isolated virus strain which is substantially the same virus strain as identified, by the method of item 1 above, as the attenuated varicella virus Oka strain or a strain derived therefrom capable of functioning as an attenuated varicella live vaccine virus.

3. An attenuated varicella virus live vaccine comprising, as an active ingredient, an isolated virus strain which is substantially the same virus strain as identified, by the method of item 1 above, as the attenuated varicella virus Oka strain or a strain derived therefrom capable of functioning as an attenuated varicella live vaccine virus.

4. An attenuated varicella virus Oka strain antigen comprising a contiguous sequence of at least 3 amino acids selected from the amino acid sequence of SEQ ID NO. 4.

5. A pair of primers selected from the group consisting of the following (a) to (d):

(a) a pair of primer (1) of SEQ ID NO: 5 and primer (3) of SEQ ID NO: 7;

(b) a pair of primer (1) of SEQ ID NO: 5 and primer (4) of SEQ ID NO: 8;

(c) a pair of primer (2) of SEQ ID NO: 6 and primer (3) of SEQ ID NO: 7; and (d) a pair of primer (PS1) of SEQ ID NO: 9 and primer (PS2) of SEQ ID NO: 10.

Hereinbelow, the present invention is described in detail.

In the present invention, with respect to the nucleotide sequences, A represents adenine, C represents cytosine, G represents guanine and T represents thymine.

In the present invention, with respect to the amino acid sequences, Ala represents an alanine residue, Arg represents an arginine residue, Asn represents an asparagine residue, Asp represents an aspartic acid residue, Cys represents a cysteine residue, Gln represents a glutamine residue, Glu represents a glutamic acid residue, Gly represents a glycine residue, His represents a histidine residue, Ile represents an isoleucine residue, Leu represents a leucine residue, Lys represents a lysine residue, Met represents a methionine residue, Phe represents a phenylalanine residue, Pro represents a proline residue, Ser represents a serine residue, Thr represents a threonine residue, Trp represents a tryptophan residue, Tyr represents a tyrosine residue and Val represents a valine residue.

(1) Preparation of the HK Fragment and the EP Fragment, and Measurements of Sizes Thereof The VZV genomic DNA is extracted and purified from the cells infected with the attenuated Oka strain virus, or with vesicle fluid and the like obtained from the naturally infected varicella patient. The extracted DNA is digested with either HpaI or EcoRI, and each of the sizes of the resultant DNA fragments is measured by agarose gel electrophoresis. For propagating the VZV, WI-38 cells and MRC-cells can be used. It is preferred that the vesicle fluid used as a sample for amplifying and preparing a viral genomic DNA of a fresh wild-type strain is obtained from a naturally infected patient within 3 days after the onset of varicella.

(2) Preparation of PCR Primers

A pair of polynucleotide strands consisting of contiguous sequences of about 15 to 30 nucleotides are prepared by a DNA synthesizer, wherein one polynucleotide strand corresponds to the 5'-terminal sequence of the desired region of one of the strands of the VZV genomic DNA to be amplified by PCR, and the other polynucleotide strand corresponds to that of the complementary strand of the above-mentioned strand of the VZV genomic DNA (for example, a sense strand and an antisense strand). The prepared polynucleotide strands are simultaneously used as the PCR primers. The prior art mentioned under "Prior Art" of the specification can be consulted when designing the nucleotide sequences of the polynucleotides for the PCR primers. However, the pairs of primers of the present invention are preferably used. The DNA fragments of a varicella virus genomic DNA analyzed for identifying the attenuated varicella virus Oka strain or a strain derived therefrom are obtained with ease and high accuracy.

(3) Preparation of Fragments Respectively Corresponding to the R2-regions, Determination of Sizes Thereof, and the Analysis of Nucleotide Sequences Thereof After extracting a VZV genomic DNA directly from a vesicle fluid in the above-mentioned manner, the R2-487 region and R2-1764 region of the extracted DNA are individually amplified by PCR. The size of each of the amplified DNA fragments is determined by agarose gel electrophoresis. The nucleotide sequence can be analyzed by the conventional methods, for example, Dideoxy method, and a method using Cycle Sequence Kit (manufactured and sold by TAKARA SHUZO Co. Ltd., Japan).

With respect to the entire coding region of VZV Gene14, the DNA can be prepared and analyzed in substantially the same manner as mentioned above. The nucleotide sequence of the entire coding region of Gene14 of the attenuated varicella virus Oka strain is shown in SEQ ID NO. 3. This sequence has been elucidated and is disclosed for the first time by the inventors of the present invention.

R2 is a repetitive sequence found in the above-mentioned Gene14, and R2 is contained in both the HK fragment and the EP fragment (see FIG. 1). Further, the amplified R2-1764 region can also be analyzed by RFLP using the restriction enzyme AccIII.

(4) Preparation of a Fragment Corresponding to the Restriction Enzyme PstI Site Region, and Determination of the Absence or Presence of a Restriction Enzyme PstI Cleavage Site After extracting the VZV genomic DNA directly from a vesicle fluid in the above-mentioned manner, the PstI site region (647 bp) of the extracted DNA is amplified by PCR. The amplified DNA fragment is digested by the restriction enzyme PstI and subjected to agarose gel electrophoresis to determine whether the PstI site region consisting of 647 bp is cleaved into two parts having sizes of 290 bp and 357 bp, respectively. The cleavage of the PstI site region into two parts confirms the existence of a PstI cleavage site in the PstI site region. The genomic DNA of the attenuated Oka strain lacks a PstI cleavage site in the PstI site region thereof and, therefore, the amplified DNA fragment is not cleaved into two parts.

(5) PCR-SSCP

The R2-487 region of the VZV genomic DNA is amplified by PCR using PCR primers labeled with $^{32}$P at their respective 5'-termini, thereby obtaining labeled DNA fragments. Each amplified DNA fragment is subjected to polyacrylamide gel electrophoresis, and the electrophoretic mobility of the fragment is compared with that of the R2-487 region of the attenuated Oka strain.

(6) Vaccine Comprising the Attenuated Oka Strain

The attenuated Oka strain virus or a virus derived therefrom which is identified by the present invention is suitable for the active ingredient of the varicella vaccine, and such a strain can be provided as a varicelia vaccine.

(7) gpV of the Attenuated Varicella Virus Oka Strain Which can be Used as an Antigen for Diagnosis As apparent from FIGS. 2 and 3, the attenuated varicella Oka strain virus identified by the present invention comprises an amino acid sequence (shown in SEQ ID NO. 4) which is specific for the attenuated varicella virus Oka strain. Therefore, gpV (glycoprotein V) coded by Gene14 of the attenuated varicella virus Oka strain genome can be used advantageously, for example, as an antigen for diagnosis. For example, the necessity of vaccination can be determined from an intracutaneous reaction using the antigen of the present invention. The attenuated varicella virus antigen of the present invention comprises a contiguous sequence of 3 or more amino acids, preferably 5 amino acids, more preferably 7 amino acids selected from the amino acid sequence of SEQ ID NO. 4.

BEST MODE FOR CARRYING OUT THE INVENTION

Hereinbelow, the present invention will be described in more detail with reference to the following Example, but they should not be construed as limiting the scope of the present invention.

EXAMPLE 1

Kawaguchi strain which is a wild-type VZV strain and the fresh wild-type strains respectively isolated from the vesicle fluids of 9 patients naturally infected with varicella (10 samples in total) were tested as follows. The attenuated Oka strain was used as a control, and the results of the tests with respect to the 10 samples were compared with the results of the tests with respect to the attenuated Oka strain.

Test (1) Determination of the Size of the HK Fragment

The attenuated Oka strain, the Kawaguchi strain and the 9 samples of vesicle fluids respectively obtained from the naturally infected varicella patients, were individually inoculated into MRC-5 cells to obtain infected cells, and the infected cells were cultured. Each of the cell cultures ($10^6$ cells) was subjected to low-speed centrifugation at 400×g at 4° C. for 5 minutes to thereby collect the infected cells, and the collected cells were freeze-thawed. Each of the collected cells was individually suspended in 5.0 ml of lysis buffer mentioned below, and treated with 50 μg of each of DNase I and RNase A at 37° C. for 30 minutes, followed by cooling in ice for 10 minutes. Then, to each of the resultant mixtures was added 2.5 ml of trichlorotrifluoroethane and vigorously agitated for 6 minutes, followed by low-speed centrifugation at 400×g at 4° C. for 15 minutes to thereby obtain a supernatant. Each of the obtained supernatants was individually layered on a discontinuous density gradient double-layer composition consisting of 2 layers of 7.5 ml of lysis buffer which respectively contain 5% (V/V) and 40% (V/V) of glycerol, and the resultant material was ultracentrifuged at 100,000×g at 4° C. for 70 minutes, thereby obtaining a precipitate. Each of the obtained precipitates was resuspended in 0.5 ml of STE buffer {1% (W/V) SDS (sodium dodecyl sulfate; 0.05 mM Tris-HCl buffer (pH 7.4); and 10 mM EDTA (2 Na)}, and treated with 500 μg of proteinase K at 65° C. for 3 hours. The resultant mixture was purified by repeating phenol extraction 3 times using an aqueous saturated phenol, followed by ethanol precipitation at −70° C. As a result, the genomic DNA of each of the 10 sample VZV viruses including the Kawaguchi strain and the genomic DNA of the attenuated Oka strain were obtained.

Composition of the Lysis Buffer

Solutes contained in 50 mM Tris-HCl buffer {pH 7.4; Tris is "Tris(hydroxymethyl)aminomethane"} and the concentrations thereof are as follows:

3 mM calcium chloride;

5 mM magnesium acetate;

125 mM potassium chloride;

1 mM EDTA (2Na) (disodium ethylenediaminetetraacetate);

1 mM DTT (dithiothreitol);

0.5% (W/V) SDC (sodium deoxycholate) and 0.5% (W/V) NONIDET P-40 (Octylphenoxyl Polyethoxy ethanol) ( manufactured and sold by Sigma Chemical Company, USA).

Each of the genomic DNAs prepared above was digested with the restriction enzyme HpaI, and the size of each of the obtained DNA fragments (HK fragments) was measured by agarose gel electrophoresis in a 0.5% (W/V) agarose gel. As a result, it was found that the size of the HK fragment of the attenuated Oka strain is 3231 bp, and only 3 samples out of the 10 samples tested had the HK fragment having the same size as that of the attenuated Oka strain.

Test (2) Determination of the Size of the EP Fragment

With respect to each of the above-mentioned samples and control, a DNA fragment (EP fragment) was obtained by treating the genomic DNA with the restriction enzyme and the size of the obtained fragment was measured by electrophoresis in substantially the same manner as in Test (1) above, except that the restriction enzyme EcoRI was used instead of HpaI. As a result, it was found that the size of the EP fragment of the attenuated Oka strain is 1749 bp, and only 3 samples out of the 10 samples tested had the EP fragment having the same size as that of the attenuated Oka strain.

Test (3) Determination of the Size and Nucleotide Sequence of the R2-487 Region

The respective genomic DNA fragments of the attenuated Oka strain and Kawaguchi strain were individually prepared from the culture media of the cells infected with the respective strains. The genomic DNA of each of the 9 fresh wild-type strains was directly prepared from the vesicle fluids of the patients. Specifically, VZV genomic DNA was solubilized by treating the vesicle fluid with guanidine thiocyanate in a final concentration of 5.5 M. The solubilized genomic DNA was subjected to a phenol extraction with phenol and then subjected to chloroform/isoamylalcohol extraction, followed by purification by isopropyl alcohol precipitation to thereby obtain a genomic DNA of the fresh wild-type strain.

The R2-487 regions of the above-obtained genomic DNAs were amplified by PCR using the PCR primers (2) and (3) to obtain R2-487 fragments. The size of each of the obtained R2-487 regions was determined by agarose gel electrophoresis in a 4% (W/V) agarose gel. As a result, it was found that the size of the R2-487 region of the attenuated Oka strain is 487 bp, and only 5 samples out of the 10 samples tested had the R2-487 region having the same size as that of the attenuated Oka strain.

Further, the nucleotide sequence of each of the R2-487 regions was determined by Cycle Sequence Kit (manufactured and sold by TAKARA SHUZO Co. Ltd., Japan; Manual Code No. R014). The nucleotide sequences of the R2-487 regions of the samples were individually compared with the nucleotide sequence of the attenuated Oka strain to determine the DNA homology between the nucleotide sequences, and also, the amino acid sequences of the R2-487 regions of the samples which were obtained by translating the nucleotide sequences in accordance with the universal code were individually compared with that of the Oka strain to determine the homology between the amino acid sequences. The determination was performed by a computer software for gene analysis {GENETYX (ver. 9.0)(A computer Software for analyzing genes and proteins; manufactured and sold by Software Development Co., Ltd., Japan}. The nucleotide sequence and amino acid sequence of the R2-487 region of the attenuated Oka strain are shown in SEQ ID NO. 1.

The comparison between the nucleotide sequence of the R2-487 region of the attenuated Oka strain and the nucleotide sequence of each of the 10 samples including the Kawaguchi strain shows that a difference in nucleotides was found with respect to 4 or more nucleotides in the R2-487 region of each of the samples, and that this difference in the nucleotides was accompanied by a change in amino acids (coded by 162 codons, i.e., 162 codons=487 bp/3). Thus, the homology between the amino acid sequence of the attenuated Oka strain and that of each of the 10 samples was less than 98% {i.e., 487 bp/3=162 codons; [(162 codons−4 different codons)/162 codons]×100=97.5% <98%}.

Test (4) Determination of the Size of the R2-1764 Region

The genomic DNA of each of the viruses was prepared in substantially the same manner as mentioned in Test (3) above, and each of the R2-1764 regions of the genomic DNAs was individually amplified by PCR using the PCR primers (1) and (3), to thereby obtain the R2-1764 fragments. Each of the obtained R2-1764 fragments was digested with the restriction enzyme AccIII, and the size of each of the digested DNA fragments was determined by agarose gel electrophoresis in a 4% (W/V) agarose gel. As a result, it was found that the R2-1764 fragment of the attenuated Oka strain is cleaved into two parts having sizes of 1208 bp and 556 bp, respectively, and only 5 samples out of the 10 samples tested showed the same restriction pattern as that of the attenuated Oka strain.

Test (5) Determination of the Absence or Presence of a Restriction Enzyme PstI Cleavage Site The respective genomic DNA fragments of the attenuated Oka strain and Kawaguchi strain were individually prepared from the culture media of the cells infected with the respective strains. The genomic DNA of each of the 9 fresh wild-type strains was directly prepared from the vesicle fluids of the patients. Specifically, the VZV genomic DNA was obtained in substantially the same manner as mentioned in Test (3) above.

The PstI site region (647 bp) of each of the above-prepared genomic DNAS was individually amplified by PCR using the PCR primers (PS1) and (P2). Each of the PCR products was treated with the restriction enzyme PstI, followed by agarose gel electrophoresis in a 4% (W/V) agarose gel to determine the absence or presence of a restriction enzyme PstI cleavage site. As a result, it was found that the PstI site fragment (647 bp) of each of the attenuated Oka strain and Kawaguchi strain was not cleaved into two parts, thus confirming the absence of the PstI cleavage site. The PstI site fragment of each of the other 9 samples was cleaved into two parts having sizes of 290 bp and 357 bp, respectively. By the cleavage of the PstI site region, the presence of a PstI cleavage site was confirmed.

Test (6) Analysis by PCR-SSCP

The R2-487 region of each of the 10 samples and control was amplified and prepared in substantially the same manner as mentioned in Test (3) above, except that the PCR primers (2) and (3) individually labeled with $^{32}P$ at respective 5' termini thereof were used instead of the non-labeled primers. Each of the PCR products was denatured by heating at 95° C. for 2 minutes and then, subjected to polyacrylamide gel electrophoresis in a 5% (W/V) polyacrylamide gel to thereby determine the electrophoretic mobility of each of the PCR products. As a result, it was found that none of the PCR products prepared from the genomic DNAs of the samples exhibited substantially the same electrophoretic mobility as the PCR product prepared from the genomic DNA of the attenuated Oka strain, and it was confirmed that none of the 10 sample virus strains are the attenuated Oka strain virus.

Test (7) Analysis of the Nucleotide Sequence of Gene14 of the Attenuated Oka Strain Genomic DNA A fragment corresponding to the entire coding region of Gene14 was prepared from the genomic DNA of the attenuated Oka strain by PCR using the PCR primers (1) and (4). The nucleotide sequence of the amplified DNA was analyzed by a DNA sequencer (manufactured and sold by LI-cor, USA). The nucleotide sequence of the entire coding region of Gene14 of the attenuated Oka strain determined above is shown in SEQ ID NO. 3.

Further, the amino acid homology between the amino acid sequence of SEQ ID NO. 4 and each of the sequences disclosed in the prior art (Davison and Scott, Journal of General Virology, 67, 1759–1816, 1986; and Kinchington et al., Journal of Virology, 59, 660–668, 1986) was analyzed in substantially the same manner as mentioned in Test (3) above. The results are shown in FIGS. 2 and 3 and 2B. The comparison between the amino acid sequences shown in FIG. 2B shows that the differences in 8 amino acids (for Davison et al.) and 9 amino acids (for Kinchington) were found between the amino acid sequences and, therefore, the amino acid homology between the amino acid sequence of the attenuated Oka strain and each of the prior art sequences was less than 99% {i.e., [(560 a.a.−8 a.a.)/560 a.a.]×100= 98.6% for Davison, and [(560 a.a.−9 a.a.)/560 a.a.]×100= 98.4% for Kinchington}. Further, it was confirmed that both of the two VZV strains disclosed in the prior art had a restriction enzyme PstI cleavage site mentioned in Test (5) above.

The results of Tests (1) to (7) are summarized in Table 2 below.

TABLE 2

| Specific characteristics satisfied by the attenuated Oka strain | Number of samples which do not satisfy the characteristics (denominator is total number of different samples) |
|---|---|
| Size of HK fragment [3231 bp] | 7/10 |
| Size of EP fragment [1749 bp] | 7/10 |
| R2-1764 region | |
| Size of AccIII fragment [1764 bp→1208 bp + 556 bp] | 5/10 |
| R2-487 region | |
| Size [487 bp] | 5/10 |
| PCR-SSCP [electrophoretic mobility as seen in the gel] | 10/10 |
| Amino acid sequence [homology: 98% or more] | 10/10 (less than 98%) |
| PstI site region [647 bp] | |
| PstI fragment [absent, i.e. fragment size = 647 bp] | [present, i.e., 647 bp→ 290 bp + 357 bp] |
| PstI restriction [absent] | 9/10 (present) |
| Gene14 coding region [1680 bp] | |
| Number of amino acid residues (560) Amino acid sequence [homology: 99% or more] | 2/2 (less than 99%) |

As apparent from the above, by determining whether or not all of the above-mentioned 8 characteristics are satisfied, the attenuated Oka strain can be distinguished from other VZV strains and identified with extremely high accuracy.

INDUSTRIAL APPLICABILITY

According to the method of the present invention, an exact quality control and quality assurance of the attenuated varicella live vaccines used today in the production thereof is achieved. Further, exact and advantageous techniques which can be used in researches in the field of epidemiology of varicella and zoster, including a tracing of the effects of the vaccine and a PMS are provided. Consequently, the present invention provides an exact and very effective measure for preventing varicella and zoster, which contributes to the health of human beings.

We claim:

1. A method for identifying the attenuated varicella virus Oka strain or a strain derived therefrom which functions as an effective component of an attenuated variceila vaccine, which comprises:

analyzing a genomic DNA and DNA fragments thereof present in a sample of varicella virus;

determining whether the analyzed genomic DNA and DNA fragments thereof of said sample of varicella virus satisfy eight characteristics (A1) to (A8) defined below; and identifying said sample of varicella virus as the attenuated varicella virus Oka strain or a strain derived therefrom which functions as an effective component of an attenuated varicella live vaccine when said sample satisfies all of the following eight characteristics (A1) to (A8):

(A1) the size of the K fragment obtained by digesting the varicella virus genomic DNA with the restriction enzyme HpaI is 3231 bp;

(A2) the size of the P fragment obtained by digesting the varicella virus genomic DNA with the restriction enzyme EcoRI is 1749 bp;

(A3) when a DNA fragment which is amplified from the varicella virus genomic DNA by PCR using the PCR primer 1 (SEQ ID NO. 3) and the PCR primer 3 (SEQ ID NO. 5) is treated with the restriction enzyme AccIII, the DNA fragment is cleaved into two parts having sizes of 1208 bp and 556 bp, respectively;

(A4) a DNA fragment which is amplified from the varicella virus genomic DNA by PCR using the PCR primer 2 (SEQ ID NO. 4) and the PCR primer 3 (SEQ ID NO. 5) has a size of 487 bp;

(A5) the varicella virus genomic DNA and the attentuated varicella virus Oka strain genomic DNA exhibit substantially the same electrophoretic mobility with respect to a DNA fragment determined by PCR-SSCP wherein the PCR primer 2 (SEQ ID NO. 4) and the PCR primer 3 (SEQ ID NO. 5) are used in the PCR of said PCR-SSCP;

(A6) a DNA fragment which is amplified from the varicella virus genomic DNA by PCR using the PCR primer PS1 (SEQ ID NO. 7) and the PCR primer PS2 (SEQ ID NO. 8) lacks a restriction enzyme PstI cleavage site;

(A7) the homology between the 162 amino acid sequence coded by the 487 bp DNA fragment amplified from the varicella virus genomic DNA by PCR using the PCR primer 2 (SEQ ID NO. 4) and the PCR primer 3 (SEQ ID NO. 5), and the 162 amino acid sequence of SEQ ID NO. 1 is 98 to 100%, wherein the percent homology is represented by the following formula (1):

$$\{(162-n)/162\times100 \qquad (1)$$

wherein n represents the number of different amino acids; and (A8) the homology between the 560 amino acid sequence coded by the entire coding region of Gene14, and the 560 amino acid sequence of SEQ ID NO. 2 is 99 to 100%, wherein the percent homology is represented by the following formula (2):

$$\{(560-n)/560\}\times100 \qquad (2)$$

wherein n represents the number of different amino acids.

2. A pair of primers selected from the group consisting of the following (a) to (d):

(a) a pair of primer (1) of SEQ ID NO:5 and primer (3) of SEQ ID NO:7;

(b) a pair of primer (1) of SEQ ID NO:5 and primer (4) of SEQ ID NO:8;

(c) a pair of primer (2) of SEQ ID NO:6 and primer (3) of SEQ ID NO:7; and (d) a pair of primer (PS1) of SEQ ID NO:9 and primer (PS2) of SEQ ID NO:10.

3. A method for the quality control of an attenuated live varicella vaccine, which comprises performing the method of claim 1 wherein the vaccine is identified as an effective component of an attenuated live vaccine if the vaccine satisfies characteristics (A1) to (A8).

* * * * *

UNITED STATES PATENT AND TRADEMARK OFFICE
CERTIFICATE OF CORRECTION

PATENT NO. : 6,093,535
DATED : July 25, 2000
INVENTOR(S): Chisato MORI et al.

It is certified that error appears in the above-identified patent and that said Letters Patent are hereby corrected as shown below:

Title page, item "[54]", please change the title from "METHOD FOR IDENTIFYING ATTENUATED CHICKENPOX VIRUS OKA STRAIN OR STRAIN ORIGINATING THEREIN AND ACCEPTABLE AS ATTENUATED CHICKENPOX VACCINE VIRUS" to -- METHOD FOR IDENTIFYING THE ATTENUATED VARICELLA VIRUS OKA STRAIN OR A STRAIN DERIVED THEREFROM --.

Signed and Sealed this

Twenty-second Day of May, 2001

Attest:

NICHOLAS P. GODICI

Attesting Officer   Acting Director of the United States Patent and Trademark Office

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
       (A) LENGTH: 487 base pairs
       (B) TYPE: nucleic acid
       (C) STRANDEDNESS: double
       (D) TOPOLOGY: linear (ii) MOLECULE TYPE: DNA (genomic)

(vi) ORIGINAL SOURCE:
       (A) ORGANISM: varicella-zoster virus
       (B) STRAIN: attenuated varicella virus Oka strain (ix) FEATURE:
       (A) NAME/KEY: CDS
       (B) LOCATION: 1..486

(xi) SEQUENCE DESCRIPTION: SEQ ID NO:1:

```
TCG ACT GAA TCT CAA CCC ACA CCC GTA AGT ATA ATT GAA TTA TAT ACC        48
Ser Thr Glu Ser Gln Pro Thr Pro Val Ser Ile Ile Glu Leu Tyr Thr
  1               5                  10                  15

TCG GCC GCT TCC CGA AAG CCC GAT CCC GCC GTC GCG CCC ACC TCG GCC        96
Ser Ala Ala Ser Arg Lys Pro Asp Pro Ala Val Ala Pro Thr Ser Ala
            20                  25                  30

GCT TCC CGA AAG CCC GAT CCC GCC GTC GCG CCC ACC TCG GCC GCT TCC       144
Ala Ser Arg Lys Pro Asp Pro Ala Val Ala Pro Thr Ser Ala Ala Ser
        35                  40                  45

CGA AAG CCC GAT CCC GCC GTC GCG CCC ACC TCG GCC GCT TCC CGA AAG       192
Arg Lys Pro Asp Pro Ala Val Ala Pro Thr Ser Ala Ala Ser Arg Lys
    50                  55                  60

CCC GAT CCC GCC GTC GCG CCC ACC TCG GCC GCT ACC CGA AAT CCC GAT       240
Pro Asp Pro Ala Val Ala Pro Thr Ser Ala Ala Thr Arg Asn Pro Asp
 65                  70                  75                  80

CCC GCC GTC GCG CCC ACC TCG GCC GCT TCC CGA AAT CCC GAT CCC GCC       288
Pro Ala Val Ala Pro Thr Ser Ala Ala Ser Arg Asn Pro Asp Pro Ala
                85                  90                  95

GTC GCG CCC ACC TCG GCC GCT TCC CGA AAT CCC GAT CCC GCC GTC GCG       336
Val Ala Pro Thr Ser Ala Ala Ser Arg Asn Pro Asp Pro Ala Val Ala
            100                 105                 110

CCC ACC TCG GCC GCT ACC CGA AAG CCC GAT CCC GCA GCC AAC GCC CAA       384
Pro Thr Ser Ala Ala Thr Arg Lys Pro Asp Pro Ala Ala Asn Ala Gln
        115                 120                 125

CAT TCA CAA CCA CCT TTT CTA TTT GAA AAT ATA CAA TGC GTT CAC GGC       432
His Ser Gln Pro Pro Phe Leu Phe Glu Asn Ile Gln Cys Val His Gly
    130                 135                 140

GGA ATA CAA TCC ATA CCC TAT TTT CAC ACA TTT ATC ATG CCT TGT TAC       480
Gly Ile Gln Ser Ile Pro Tyr Phe His Thr Phe Ile Met Pro Cys Tyr
145                 150                 155                 160

ATG CGT C                                                             487
Met Arg
```

(2) INFORMATION FOR SEQ ID NO:2:

(i) SEQUENCE CHARACTERISTICS:
(A) LENGTH: 162 amino acids
(B) TYPE: amino acid
(D) TOPOLOGY: linear -continued

```
    (ii) MOLECULE TYPE: protein (vi) ORIGINAL SOURCE:
         (A) ORGANISM: varicella-zoster virus
         (B) STRAIN: attenuated varicella virus Oka strain (xi) SEQUENCE DESCRIPTION: SEQ ID NO:2:

Ser Thr Glu Ser Gln Pro Thr Pro Val Ser Ile Ile Glu Leu Tyr Thr
 1               5                  10                  15

Ser Ala Ala Ser Arg Lys Pro Asp Pro Ala Val Ala Pro Thr Ser Ala
                20                  25                  30

Ala Ser Arg Lys Pro Asp Pro Ala Val Ala Pro Thr Ser Ala Ala Ser
            35                  40                  45

Arg Lys Pro Asp Pro Ala Val Ala Pro Thr Ser Ala Ala Ser Arg Lys
        50                  55                  60

Pro Asp Pro Ala Val Ala Pro Thr Ser Ala Ala Thr Arg Asn Pro Asp
 65                  70                  75                  80

Pro Ala Val Ala Pro Thr Ser Ala Ala Ser Arg Asn Pro Asp Pro Ala
                85                  90                  95

Val Ala Pro Thr Ser Ala Ala Ser Arg Asn Pro Asp Pro Ala Val Ala
            100                 105                 110

Pro Thr Ser Ala Ala Thr Arg Lys Pro Asp Pro Ala Ala Asn Ala Gln
        115                 120                 125

His Ser Gln Pro Pro Phe Leu Phe Glu Asn Ile Gln Cys Val His Gly
130                 135                 140

Gly Ile Gln Ser Ile Pro Tyr Phe His Thr Phe Ile Met Pro Cys Tyr
145                 150                 155                 160

Met Arg (2) INFORMATION FOR SEQ ID NO:3:

(i) SEQUENCE CHARACTERISTICS:
        (A) LENGTH: 1683 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: varicella-zoster virus
         (B) STRAIN: attenuated varicella virus Oka strain (ix) FEATURE:
         (A) NAME/KEY: CDS
         (B) LOCATION: 1..1683

(xi) SEQUENCE DESCRIPTION: SEQ ID NO:3:

ATG AAG CGG ATA CAA ATA AAT TTA ATT TTA ACG ATC GCG TGT ATA CAA      48
Met Lys Arg Ile Gln Ile Asn Leu Ile Leu Thr Ile Ala Cys Ile Gln
            165                 170                 175

TTA TCG ACT GAA TCT CAA CCC ACA CCC GTA AGT ATA ATT GAA TTA TAT      96
Leu Ser Thr Glu Ser Gln Pro Thr Pro Val Ser Ile Ile Glu Leu Tyr
180                 185                 190

ACC TCG GCC GCT TCC CGA AAG CCC GAT CCC GCC GTC GCG CCC ACC TCG     144
Thr Ser Ala Ala Ser Arg Lys Pro Asp Pro Ala Val Ala Pro Thr Ser
195                 200                 205                 210

GCC GCT TCC CGA AAG CCC GAT CCC GCC GTC GCG CCC ACC TCG GCC GCT     192
Ala Ala Ser Arg Lys Pro Asp Pro Ala Val Ala Pro Thr Ser Ala Ala
            215                 220                 225

TCC CGA AAG CCC GAT CCC GCC GTC GCG CCC ACC TCG GCC GCT TCC CGA     240
Ser Arg Lys Pro Asp Pro Ala Val Ala Pro Thr Ser Ala Ala Ser Arg
```

-continued

| | 230 | | | | | 235 | | | | | 240 | | | |
|---|---|---|---|---|---|---|---|---|---|---|---|---|---|---|
| AAG | CCC | GAT | CCC | GCC | GTC | GCG | CCC | ACC | TCG | GCC | GCT | ACC | CGA | AAT | CCC | 288 |
| Lys | Pro | Asp | Pro | Ala | Val | Ala | Pro | Thr | Ser | Ala | Ala | Thr | Arg | Asn | Pro | |
| | | | 245 | | | | | 250 | | | | | 255 | | | |

```
AAG CCC GAT CCC GCC GTC GCG CCC ACC TCG GCC GCT ACC CGA AAT CCC       288
Lys Pro Asp Pro Ala Val Ala Pro Thr Ser Ala Ala Thr Arg Asn Pro
            245                 250                 255

GAT CCC GCC GTC GCG CCC ACC TCG GCC GCT TCC CGA AAT CCC GAT CCC       336
Asp Pro Ala Val Ala Pro Thr Ser Ala Ala Ser Arg Asn Pro Asp Pro
        260                 265                 270

GCC GTC GCG CCC ACC TCG GCC GCT TCC CGA AAT CCC GAT CCC GCC GTC       384
Ala Val Ala Pro Thr Ser Ala Ala Ser Arg Asn Pro Asp Pro Ala Val
275                 280                 285                 290

GCG CCC ACC TCG GCC GCT ACC CGA AAG CCC GAT CCC GCA GCC AAC GCC       432
Ala Pro Thr Ser Ala Ala Thr Arg Lys Pro Asp Pro Ala Ala Asn Ala
            295                 300                 305

CAA CAT TCA CAA CCA CCT TTT CTA TTT GAA AAT ATA CAA TGC GTT CAC       480
Gln His Ser Gln Pro Pro Phe Leu Phe Glu Asn Ile Gln Cys Val His
        310                 315                 320

GGC GGA ATA CAA TCC ATA CCC TAT TTT CAC ACA TTT ATC ATG CCT TGT       528
Gly Gly Ile Gln Ser Ile Pro Tyr Phe His Thr Phe Ile Met Pro Cys
            325                 330                 335

TAC ATG CGT CTA ACG ACC GGA CAA CAG GCG GCC TTT AAG CAG CAA CAA       576
Tyr Met Arg Leu Thr Thr Gly Gln Gln Ala Ala Phe Lys Gln Gln Gln
        340                 345                 350

AAA ACA TAT GAA CAA TAT TCT TTA GAT CCG GAA GGT TCA AAT ATA ACA       624
Lys Thr Tyr Glu Gln Tyr Ser Leu Asp Pro Glu Gly Ser Asn Ile Thr
355                 360                 365                 370

AGG TGG AAG TCG CTT ATA CGC CCC GAT CTT CAT ATT GAA GTT TGG TTT       672
Arg Trp Lys Ser Leu Ile Arg Pro Asp Leu His Ile Glu Val Trp Phe
            375                 380                 385

ACG CGT CAC CTT ATA GAT CCG CAC CGT CAA CTG GGC AAT GCG TTA ATA       720
Thr Arg His Leu Ile Asp Pro His Arg Gln Leu Gly Asn Ala Leu Ile
        390                 395                 400

CGC ATG CCA GAT TTA CCG GTT ATG TTA TAT AGC AAC AGT GCC GAT TTA       768
Arg Met Pro Asp Leu Pro Val Met Leu Tyr Ser Asn Ser Ala Asp Leu
            405                 410                 415

AAC TTA ATA AAC AAC CCT GAG ATA TTT ACA CAC GCT AAG GAA AAT TAT       816
Asn Leu Ile Asn Asn Pro Glu Ile Phe Thr His Ala Lys Glu Asn Tyr
        420                 425                 430

GTA ATA CCA GAT GTT AAA ACA ACG TCT GAT TTT TCT GTA ACA ATT TTA       864
Val Ile Pro Asp Val Lys Thr Thr Ser Asp Phe Ser Val Thr Ile Leu
435                 440                 445                 450

TCT ATG GAT GCT ACC ACG GAG GGA ACG TAT ATT TGG CGA GTC GTT AAT       912
Ser Met Asp Ala Thr Thr Glu Gly Thr Tyr Ile Trp Arg Val Val Asn
            455                 460                 465

ACA AAA ACT AAG AAC GTC ATA TCG GAA CAC AGT ATT ACA GTT ACA ACG       960
Thr Lys Thr Lys Asn Val Ile Ser Glu His Ser Ile Thr Val Thr Thr
        470                 475                 480

TAT TAT CGT CCA AAT ATT ACC GTT GTC GGC GAT CCA GTC TTA ACC GGA      1008
Tyr Tyr Arg Pro Asn Ile Thr Val Val Gly Asp Pro Val Leu Thr Gly
            485                 490                 495

CAG ACA TAC GCA GCC TAC TGT AAC GTA TCA AAG TAT TAT CCA CCG CAC      1056
Gln Thr Tyr Ala Ala Tyr Cys Asn Val Ser Lys Tyr Tyr Pro Pro His
        500                 505                 510

TCG GTA CGT GTT CGG TGG ACT TCA AGG TTT GGT AAC ATC GGA AAA AAT      1104
Ser Val Arg Val Arg Trp Thr Ser Arg Phe Gly Asn Ile Gly Lys Asn
515                 520                 525                 530

TTT ATA ACC GAT GCA ATA CAA GAA TAT GCC AAT GGA TTA TTT AGT TAT      1152
Phe Ile Thr Asp Ala Ile Gln Glu Tyr Ala Asn Gly Leu Phe Ser Tyr
            535                 540                 545

GTT TCG GCG GTA CGA ATT CCA CAG CAA AAA CAA ATG GAT TAC CCA CCC      1200
```

-continued

```
Val Ser Ala Val Arg Ile Pro Gln Gln Lys Gln Met Asp Tyr Pro Pro
            550                 555                 560

CCA GCC ATC CAA TGT AAT GTT TTA TGG ATT CGG GAT GGC GTC TCT AAT      1248
Pro Ala Ile Gln Cys Asn Val Leu Trp Ile Arg Asp Gly Val Ser Asn
        565                 570                 575

ATG AAA TAT TCT GCT GTC GTT ACC CCT GAC GTC TAT CCA TTT CCC AAC      1296
Met Lys Tyr Ser Ala Val Val Thr Pro Asp Val Tyr Pro Phe Pro Asn
580                 585                 590

GTG TCT ATA GGT ATT ATT GAT GGA CAC ATA GTA TGT ACG GCA AAA TGT      1344
Val Ser Ile Gly Ile Ile Asp Gly His Ile Val Cys Thr Ala Lys Cys
595                 600                 605                 610

GTG CCA CGT GGC GTT GTA CAT TTC GTA TGG TGG GTT AAC GAT TCT CCC      1392
Val Pro Arg Gly Val Val His Phe Val Trp Trp Val Asn Asp Ser Pro
            615                 620                 625

ATC AAC CAC GAA AAC AGT GAG ATT ACT GGG GTG TGT GAT CAA AAC AAA      1440
Ile Asn His Glu Asn Ser Glu Ile Thr Gly Val Cys Asp Gln Asn Lys
        630                 635                 640

CGG TTT GTA AAC ATG CAA AGT TCT TGT CCA ACA TCG GAA CTC GAC GGA      1488
Arg Phe Val Asn Met Gln Ser Ser Cys Pro Thr Ser Glu Leu Asp Gly
        645                 650                 655

CCT ATC ACC TAT TCG TGT CAT CTA GAT GGT TAC CCT AAA AAA TTC CCT      1536
Pro Ile Thr Tyr Ser Cys His Leu Asp Gly Tyr Pro Lys Lys Phe Pro
660                 665                 670

CCG TTT TCG GCC GTT TAT ACC TAC GAT GCA TCT ACC TAC GCC ACT ACA      1584
Pro Phe Ser Ala Val Tyr Thr Tyr Asp Ala Ser Thr Tyr Ala Thr Thr
675                 680                 685                 690

TTT TCC GTT GTA GCA GTT ATA ATT GGT GTG ATA TCT ATC CTT GGG ACA      1632
Phe Ser Val Val Ala Val Ile Ile Gly Val Ile Ser Ile Leu Gly Thr
            695                 700                 705

TTG GGT CTT ATC GCA GTT ATC GCA ACC CTA TGC ATC CGT TGC TGT TCA      1680
Leu Gly Leu Ile Ala Val Ile Ala Thr Leu Cys Ile Arg Cys Cys Ser
            710                 715                 720

TAA                                                                   1683
```

(2) INFORMATION FOR SEQ ID NO:4:

(i) SEQUENCE CHARACTERISTICS:
        (A) LENGTH: 560 amino acids
        (B) TYPE: amino acid
        (D) TOPOLOGY: linear (ii) MOLECULE TYPE: protein (vi) ORIGINAL SOURCE:
        (A) ORGANISM: varicella-zoster virus
        (B) STRAIN: attenuated varicella virus Oka strain (xi) SEQUENCE DESCRIPTION: SEQ ID NO:4:

```
Met Lys Arg Ile Gln Ile Asn Leu Ile Leu Thr Ile Ala Cys Ile Gln
  1               5                  10                  15

Leu Ser Thr Glu Ser Gln Pro Thr Pro Val Ser Ile Ile Glu Leu Tyr
            20                  25                  30

Thr Ser Ala Ala Ser Arg Lys Pro Asp Pro Ala Val Ala Pro Thr Ser
        35                  40                  45

Ala Ala Ser Arg Lys Pro Asp Pro Ala Val Ala Pro Thr Ser Ala Ala
    50                  55                  60

Ser Arg Lys Pro Asp Pro Ala Val Ala Pro Thr Ser Ala Ala Ser Arg
 65                  70                  75                  80

Lys Pro Asp Pro Ala Val Ala Pro Thr Ser Ala Ala Thr Arg Asn Pro
                85                  90                  95
```

-continued

```
Asp Pro Ala Val Ala Pro Thr Ser Ala Ala Ser Arg Asn Pro Asp Pro
            100                 105                 110

Ala Val Ala Pro Thr Ser Ala Ala Ser Arg Asn Pro Asp Pro Ala Val
            115                 120                 125

Ala Pro Thr Ser Ala Ala Thr Arg Lys Pro Asp Pro Ala Ala Asn Ala
            130                 135                 140

Gln His Ser Gln Pro Pro Phe Leu Phe Glu Asn Ile Gln Cys Val His
145                 150                 155                 160

Gly Gly Ile Gln Ser Ile Pro Tyr Phe His Thr Phe Ile Met Pro Cys
                165                 170                 175

Tyr Met Arg Leu Thr Thr Gly Gln Gln Ala Ala Phe Lys Gln Gln Gln
            180                 185                 190

Lys Thr Tyr Glu Gln Tyr Ser Leu Asp Pro Glu Gly Ser Asn Ile Thr
            195                 200                 205

Arg Trp Lys Ser Leu Ile Arg Pro Asp Leu His Ile Glu Val Trp Phe
            210                 215                 220

Thr Arg His Leu Ile Asp Pro His Arg Gln Leu Gly Asn Ala Leu Ile
225                 230                 235                 240

Arg Met Pro Asp Leu Pro Val Met Leu Tyr Ser Asn Ser Ala Asp Leu
                245                 250                 255

Asn Leu Ile Asn Asn Pro Glu Ile Phe Thr His Ala Lys Glu Asn Tyr
            260                 265                 270

Val Ile Pro Asp Val Lys Thr Thr Ser Asp Phe Ser Val Thr Ile Leu
            275                 280                 285

Ser Met Asp Ala Thr Thr Glu Gly Thr Tyr Ile Trp Arg Val Val Asn
            290                 295                 300

Thr Lys Thr Lys Asn Val Ile Ser Glu His Ser Ile Thr Val Thr Thr
305                 310                 315                 320

Tyr Tyr Arg Pro Asn Ile Thr Val Val Gly Asp Pro Val Leu Thr Gly
                325                 330                 335

Gln Thr Tyr Ala Ala Tyr Cys Asn Val Ser Lys Tyr Tyr Pro Pro His
            340                 345                 350

Ser Val Arg Val Arg Trp Thr Ser Arg Phe Gly Asn Ile Gly Lys Asn
            355                 360                 365

Phe Ile Thr Asp Ala Ile Gln Glu Tyr Ala Asn Gly Leu Phe Ser Tyr
            370                 375                 380

Val Ser Ala Val Arg Ile Pro Gln Gln Lys Gln Met Asp Tyr Pro Pro
385                 390                 395                 400

Pro Ala Ile Gln Cys Asn Val Leu Trp Ile Arg Asp Gly Val Ser Asn
                405                 410                 415

Met Lys Tyr Ser Ala Val Val Thr Pro Asp Val Tyr Pro Phe Pro Asn
            420                 425                 430

Val Ser Ile Gly Ile Ile Asp Gly His Ile Val Cys Thr Ala Lys Cys
            435                 440                 445

Val Pro Arg Gly Val Val His Phe Val Trp Val Asn Asp Ser Pro
            450                 455                 460

Ile Asn His Glu Asn Ser Glu Ile Thr Gly Val Cys Asp Gln Asn Lys
465                 470                 475                 480

Arg Phe Val Asn Met Gln Ser Ser Cys Pro Thr Ser Glu Leu Asp Gly
                485                 490                 495

Pro Ile Thr Tyr Ser Cys His Leu Asp Gly Tyr Pro Lys Lys Phe Pro
            500                 505                 510

Pro Phe Ser Ala Val Tyr Thr Tyr Asp Ala Ser Thr Tyr Ala Thr Thr
```

```
          515                 520                 525
Phe Ser Val Val Ala Val Ile Ile Gly Val Ile Ser Ile Leu Gly Thr
    530                 535                 540

Leu Gly Leu Ile Ala Val Ile Ala Thr Leu Cys Ile Arg Cys Cys Ser
545                 550                 555                 560
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthesized DNA PCR primer"

(xi) SEQUENCE DESCRIPTION: SEQ ID NO:5:

GATGGATATA ATCCACACCC                                                  20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthesized DNA PCR primer"

(xi) SEQUENCE DESCRIPTION: SEQ ID NO:6:

GACGCATGTA ACAAGGCATG                                                  20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthesized DNA PCR primer"

(xi) SEQUENCE DESCRIPTION: SEQ ID NO:7:

TCGACTGAAT CTCAACCCAC                                                  20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthesized DNA PCR primer"

(xi) SEQUENCE DESCRIPTION: SEQ ID NO:8:

GATGTTTCCA AATCTAACTC                                                  20

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single -continued

```
        (D) TOPOLOGY: linear (ii) MOLECULE TYPE: other nucleic acid
        (A) DESCRIPTION: /desc = "Synthesized DNA PCR primer"

(xi) SEQUENCE DESCRIPTION: SEQ ID NO:9:

AAGTTTCAGC CAACGTGCCA ATAAA                                              25

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthesized DNA PCR primer"

(xi) SEQUENCE DESCRIPTION: SEQ ID NO:10:

AGACGCGCTT AACGGAAGTA ACG                                                23
```